US011207251B2

(12) United States Patent
Malet et al.

(10) Patent No.: US 11,207,251 B2
(45) Date of Patent: Dec. 28, 2021

(54) ANTIMICROBIAL MIXTURE CONTAINING 4-(3-ETHOXY-4-HYDROXYPHENYL)BUTAN-2-ONE AND CHLORPHENESIN, AND COSMETIC COMPOSITION CONTAINING SAME

(71) Applicant: L'OREAL, Paris (FR)

(72) Inventors: Gael Malet, Chevilly Larue (FR); Sylvie Cupferman, Chevilly Larue (FR)

(73) Assignee: L'OREAL, Paris (FR)

( * ) Notice: Subject to any disclaimer, the term of this patent is extended or adjusted under 35 U.S.C. 154(b) by 170 days.

(21) Appl. No.: 16/625,327

(22) PCT Filed: Jun. 27, 2018

(86) PCT No.: PCT/EP2018/067304
§ 371 (c)(1),
(2) Date: Dec. 20, 2019

(87) PCT Pub. No.: WO2019/002396
PCT Pub. Date: Jan. 3, 2019

(65) Prior Publication Data
US 2021/0338550 A1 Nov. 4, 2021

(30) Foreign Application Priority Data

Jun. 30, 2017 (FR) ........................................ 1756153

(51) Int. Cl.
A61K 8/35 (2006.01)
A61Q 17/00 (2006.01)
A61K 8/34 (2006.01)

(52) U.S. Cl.
CPC ............... A61K 8/35 (2013.01); A61K 8/345 (2013.01); A61Q 17/005 (2013.01); A61K 2800/5922 (2013.01)

(58) Field of Classification Search
CPC .... A23L 3/3499; A23L 3/3481; A23L 3/3526; A61Q 19/08; A61Q 19/02; A61Q 19/00; A61Q 17/04; A61Q 17/005; A61Q 5/006; A61Q 5/02; A61Q 5/12; A61Q 15/00; A61Q 11/00; A61Q 13/00; A61Q 17/00; A61Q 19/004; A61Q 19/008; A61Q 1/10; A61Q 5/00; A61Q 5/06; A61Q 7/00; A61Q 19/005; A61Q 19/007; A61Q 19/06; A61Q 19/10; A61Q 1/02; A61Q 1/12; A61Q 19/002; A61Q 19/04; A61Q 1/04; A61Q 1/06; A61Q 1/08; A61Q 1/14; A61Q 3/02; A61Q 5/065; A61Q 9/02; A61Q 9/04; A61Q 5/04; A61Q 5/10; A61Q 1/00; A61P 17/00; A61P 31/04; A61P 29/00; A61P 31/00; A61P 17/10; A61P 31/10; A61P 43/00; A61P 35/00; A61P 3/10; A61P 17/02; A61P 33/00; A61P 33/02; A61P 17/06; A61P 17/14; A61P 17/18; A61P 19/08; A61P 9/10; A61P 17/04; A61P 19/02; A61P 27/02; A61P 31/12; A61P 3/04; A61P 11/00; A61P 17/12; A61P 25/04; A61P 35/02; A61P 37/08; A61P 9/12; A61P 13/02; A61P 13/08; A61P 13/12; A61P 15/02; A61P 17/08; A61P 19/00; A61P 1/00; A61P 1/02; A61P 1/12; A61P 21/00; A61P 21/04; A61P 27/16; A61P 37/00; A61P 3/00; A61P 41/00; A61P 9/00; A61P 11/14; A61P 15/00; A61P 15/04; A61P 15/08; A61P 15/18; A61P 17/16; A61P 19/10; A61P 1/04; A61P 1/08; A61P 1/16; A61P 1/18; A61P 25/00; A61P 25/16; A61P 25/28; A61P 27/00; A61P 27/06; A61P 27/12; A61P 31/02; A61P 33/14; A61P 37/02; A61P 37/06; A61P 3/06; A61P 3/08; A61P 5/14; A61P 5/16; A61P 5/34; A61P 7/02; A01N 35/02; A01N 31/02; A01N 47/44; A01N 43/40; A01N 59/16; A01N 2300/00; A01N 37/06; A01N 37/10; A01N 37/28; A01N 31/08; A01N 37/52; A01N 31/04; A01N 31/14; A01N 33/12; A01N 37/40; A01N 39/00; A01N 43/16; A01N 31/16; A01N 47/36; A01N 33/04; A01N 25/02; A01N 33/08; A01N 59/00; A01N 65/08; A01N 65/22; A01N 65/28; A01N 65/44; A01N 43/50; A01N 35/04; A01N 37/12; A01N 37/36; A01N 37/44; A01N 43/08; A01N 37/46; A61K 8/35; A61K 8/345; A61K 2800/524; A61K 47/10; A61K 8/04; A61K 8/8123; A61K 8/8152; A61K 8/87; A61K 8/37; A61K 2800/92; A61K 8/416; A61K 8/40; A61K 8/4926; A61K 8/4946; A61K 8/88; A61K 8/41; A61K 2800/10; A61K 8/375; A61K 8/02; A61K 8/347; A61K 8/4973;
(Continued)

(56) References Cited

U.S. PATENT DOCUMENTS

2011/0152383 A1* 6/2011 Schmaus .................. A61K 8/34
514/731
2012/0251460 A1* 10/2012 Daiko ..................... A61Q 19/00
424/43

FOREIGN PATENT DOCUMENTS

JP     2008-007432 A     1/2008

* cited by examiner

Primary Examiner — Audrea B Coniglio
Assistant Examiner — Audrea Buckley
(74) Attorney, Agent, or Firm — Polsinelli PC

(57) ABSTRACT

The invention relates to an antimicrobial mixture containing 4-(3-ethoxy-4-hydroxyphenyl)butan-2-one and chlorphenesin, and also to a cosmetic composition containing such a mixture. Use in caring for, making up and cleansing keratin materials.

20 Claims, No Drawings

(58) Field of Classification Search
CPC .. A61K 8/64; A61K 8/8158; A61K 2800/592; A61K 8/062; A61K 8/34; A61K 8/42; A61K 8/44; A61K 8/9789
See application file for complete search history.

ANTIMICROBIAL MIXTURE CONTAINING 4-(3-ETHOXY-4-HYDROXYPHENYL)BUTAN-2-ONE AND CHLORPHENESIN, AND COSMETIC COMPOSITION CONTAINING SAME

CROSS REFERENCE TO RELATED APPLICATIONS

This application is a National Phase filing under 35 U.S.C. § 371 of PCT/EP2018/067304 filed on 27 Jun. 2018; which application in turn claims priority to Application No. 1756153 filed in France on 30 Jun. 2017. The entire contents of each application are hereby incorporated by reference.

The present invention relates to an antibacterial mixture containing 4-(3-ethoxy-4-hydroxyphenyl)butan-2-one and chlorphenesin, and also to a cosmetic composition containing such a mixture.

4-(3-Ethoxy-4-hydroxyphenyl)butan-2-one (ketone compound) is a useful substance as a preserving agent for cosmetic compositions, for protecting the compositions against microbial contamination, as described in the patent application WO 2011/039445.

However, it is desirable to be able to incorporate said ketone compound in reduced concentration in compositions, especially cosmetic or dermatological compositions, while at the same time maintaining good antimicrobial conservation performance. Combinations of the ketone compound with other compounds that have antimicrobial efficacy are thus sought for this purpose.

The inventors have discovered, unexpectedly, that the combination of 4-(3-ethoxy-4-hydroxyphenyl)butan-2-one with chlorphenesin makes it possible to obtain an antimicrobial mixture with synergistic antimicrobial activity, in particular on moulds, especially on *Aspergillus niger*. The results of Example 1 described below show the synergistic antimicrobial activity obtained with the minimum inhibitory concentration (MIC) measurements taken with several mixtures. The antimicrobial activity is considered as being synergistic when the antimicrobial mixture makes it possible to obtain a percentage of strain growth of less than or equal to 25%, or even less than or equal to 20%.

More precisely, a subject of the invention is an antimicrobial mixture comprising, or constituted by (or consisting of), 4-(3-ethoxy-4-hydroxyphenyl)butan-2-one and chlorphenesin. A subject of the invention is also a composition, especially a cosmetic or dermatological composition, comprising, in a physiologically acceptable medium, said mixture described previously.

A further subject of the invention is a process for the non-therapeutic cosmetic treatment of keratin materials, comprising the application to the keratin materials of a composition as described above. The process may be a cosmetic process for caring for or making up or cleansing keratin materials.

4-(3-Ethoxy-4-hydroxyphenyl)butan-2-one is a compound of formula:

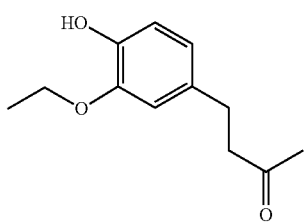

Chlorphenesin corresponds to the compound 3-(4-chlorophenoxy)-1,2-propanediol (CAS No.: 104-29-0) of formula:

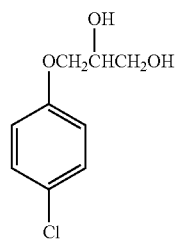

Advantageously, 4-(3-ethoxy-4-hydroxyphenyl)butan-2-one and chlorphenesin are present in said mixture in a content such that the 4-(3-ethoxy-4-hydroxyphenyl)butan-2-one/chlorphenesin weight ratio ranges from 0.1 to 0.9, preferably from 0.1 to 0.7 and preferentially from 0.15 to 0.6.

The compound 4-(3-ethoxy-4-hydroxyphenyl)butan-2-one may be present in the composition according to the invention at an amount ranging from 0.01% to 5% by weight relative to the total weight of the composition, preferably ranging from 0.01% to 3% by weight, preferentially ranging from 0.01% to 2.5% by weight and more preferentially ranging from 0.01% to 2% by weight.

A subject of the invention is also a composition comprising, in a physiologically acceptable medium, the antimicrobial mixture described previously.

The term "physiologically acceptable medium" means a medium that is compatible with human keratin materials such as the skin, the scalp, the hair and the nails. Said medium may comprise one or more additional ingredients other than the ketone compound and chlorphenesin.

The composition may comprise at least one additional ingredient chosen from water, oils, polyols containing from 2 to 10 carbon atoms, gelling agents, surfactants, film-forming polymers, dyestuffs, fragrances, fillers, UV-screening agents, plant extracts, cosmetic and dermatological active agents, and salts.

The composition according to the invention may comprise an aqueous phase.

The composition may comprise water, which may be present at an amount ranging from 5% to 90% by weight relative to the total weight of the composition, and preferably ranging from 35% to 75% by weight.

The composition may also comprise a polyol that is water-miscible at room temperature (25° C.), especially chosen from polyols especially containing from 2 to 10 carbon atoms, preferably containing from 2 to 6 carbon atoms, such as glycerol, propylene glycol, 1,3-propanediol, butylene glycol, pentylene glycol, hexylene glycol, dipropylene glycol, diethylene glycol or diglycerol. Advantageously, the composition according to the invention comprises 1,3-propanediol, especially in a content ranging from 0.1% to 20% by weight, preferably ranging from 0.1% to 10% by weight and preferentially ranging from 0.5% to 5% by weight, relative to the total weight of the composition.

The compositions according to the invention may be in the form of oil-in-water (O/W) emulsions, water-in-oil (W/O) emulsions or multiple emulsions (triple: W/O/W or O/W/O), oily solutions, oily gels, aqueous solutions, aqueous gels, solid compositions. These compositions are prepared according to the usual methods.

The compositions according to the invention may be more or less fluid and may have the appearance of a white or coloured cream, an ointment, a milk, a lotion, a serum, a paste or a foam. They may be optionally applied to the skin in aerosol form. They may also be in solid form, for example in the form of a stick or a compact powder.

The composition according to the invention may especially be in the form of:
- a makeup product, especially for making up the skin of the face, the body, or the lips or the eyelashes;
- an aftershave gel or lotion; a shaving product;
- a deodorant (stick, roll-on or aerosol);
- a hair-removing cream;
- a body hygiene composition such as a shower gel or a shampoo;
- a pharmaceutical composition;
- a solid composition such as a soap or a cleansing bar;
- an aerosol composition also comprising a pressurized propellant;
- a hairsetting lotion, a hair-styling cream or gel, a dye composition, a permanent-waving composition, a lotion or a gel for combating hair loss, or a hair conditioner;
- a composition for caring for or cleansing the skin.

A subject of the invention is also a process for preparing a composition, especially a cosmetic or dermatological composition, comprising a step of mixing 4-(3-ethoxy-4-hydroxyphenyl)butan-2-one, chlorphenesin and one or more additional ingredients, especially cosmetic or dermatological ingredients, such as those described previously.

The invention is illustrated in greater detail in the example that follows. The amounts of the ingredients are expressed as weight percentages.

EXAMPLE 1: DETERMINATION OF THE SYNERGISTIC ANTIMICROBIAL ACTIVITY IN MIC ON THE MICROBIAL STRAIN *ASPERGILLUS NIGER*

The demonstration of a synergistic antimicrobial activity effect with a mixture of 4-(3-ethoxy-4-hydroxyphenyl)butan-2-one (referred to as substance A) and of chlorphenesin (referred to as substance B) is performed by calculating the synergy index (or FIC index) according to the following formula FIC Index=(MICa with *B*/MICa)+(MICb with *A*/MICb)

with:
- MICa with B: minimum concentration of product A in the combination A+B which makes it possible to obtain an inhibitory effect.
- MICb with A: minimum concentration of product B in the combination A+B which makes it possible to obtain the inhibitory effect.
- MICa: minimum inhibitory concentration of product A alone.
- MICb: minimum inhibitory concentration of product B alone.

This formula was described for the first time in the article by F. C. Kull, P. C. Eisman, H. D. Sylwestrowka, and R. L. Mayer, Applied Microbiology 9:538-541, 1961.

For each compound tested alone, the MIC is considered as the first concentration which makes it possible to obtain a microbial growth percentage of less than or equal to 25%.

As regards the combinations tested, MICa with b and MICb with a are the respective concentrations of A and of B in the combinations which make it possible to obtain a microbial growth percentage of less than or equal to 25%.

Interpretation of the FIC Index:

When the FIC index value is less than or equal to 1, it is considered that the combination of test compounds has a synergistic effect.

The results obtained are summarized in the following tables.

The microbial strain *Aspergillus niger* ATCC 6275, and a double-concentration Sabouraud broth liquid culture medium supplemented with polyoxyethylenated (20 OE) sorbitan monopalmitate (Tween 40 from Croda) and Phytagel© BioReagent were used (i.e. a mixture of 5 g of Phytagel+0.6 g Tween 40+60 g of Sabouraud broth).

A 96-well microplate at an incubation temperature of 32.5° C. is used.

The incubation time of the microplate is from 24 to 48 hours aerobically.

Test

For each compound:
A=4-(3-ethoxy-4-hydroxyphenyl)butan-2-one compound
B=chlorphenesin compound A 10% (weight/volume) stock solution was prepared by mixing 1 g of compound in 9 ml of aqueous 1‰ agar solution. Successive dilutions were made with the 1‰ agar solution.

Test of compounds A and B alone

50 μL of each of the daughter solutions obtained containing compound A or B are added to the microplate wells. 100 μL of Sabouraud liquid nutrient broth inoculated with the strain *Aspergillus niger* and 50 μL of aqueous 1‰ agar solution are also added thereto.

Test of compounds A and B as a mixture

50 μL of each of the daughter solutions obtained containing compound A and 50 μL of each of the daughter solutions obtained containing compound B are added to the microplate wells. 100 μL of Sabouraud liquid nutrient broth inoculated at double concentration with the strain *Aspergillus niger* are also added thereto.

Microbial Growth Control

A positive microbial growth control was also prepared. The positive microbial growth control corresponds to a mixture of 100 μL of aqueous 1‰ agar solution with 100 μL of Sabouraud liquid nutrient broth inoculated at double concentration with the strain *Aspergillus niger* in the absence of compounds A and B.

Absorbance Control of Compounds A and B Alone

An absorbance control was performed in parallel on compounds A and B alone. This control corresponds to 100 μL of double concentration sterile Sabouraud liquid nutrient broth+100 μL of double concentration compound A or B.

In the three cases (absorbance control, growth control and test), the final volume present in each of the microplate wells is 200 μL.

In the two cases (test and control), the inoculum represents the concentration of the strain *Aspergillus niger* present in the final volume of the wells (200 μL) and is between 2 and $6 \times 10^5$ cfu/ml of *Aspergillus niger*.

The minimum inhibitory concentration (MIC) of each compound A and B alone and in combination was determined in a known manner by means of optical density measurements at a wavelength of 620 nm.

The following results were obtained:

| concentrations tested (in weight %) | 0 A | 0.0625 A | 0.125 A | 0.25 A |
|---|---|---|---|---|
| 0 B |  | 79 | 41 | 5 |
| 0.0125 B | 71 | 46 | 26 | 2 |
| 0.25 B | 38 | 3 (FIC 0.75) | 2 (FIC 1) | 2 |
| 0.5 B | 1 | 1 | 1 | 2 |

| % MIC of A alone | % MIC of B alone | MIC of each compound as a mixture | | FIC Index | |
|---|---|---|---|---|---|
| | | A % | B % | | |
| 0.25 | 0.5 | 0.0625 | 0.25 | 0.75 Synergism | Ratio A/B = 0.25 |

The results obtained show synergistic inhibitory activity for the mixtures:
i) 0.0625% of A and 0.25% of B, i.e. ratio A/B=0.25
ii) 0.125% of A and 0.25% of B, i.e. ratio A/B=0.5

EXAMPLE 2: DETERMINATION OF THE ANTIMICROBIAL ACTIVITY OF THE ANTIMICROBIAL MIXTURE

The antimicrobial efficacy of the 4-(3-ethoxy-4-hydroxyphenyl)butan-2-one+chlorphenesin antimicrobial mixture (respective weight ratio of 0.16) was evaluated by the Challenge Test method.

Protocol

The method of the challenge test consists of an artificial contamination of the sample with microbial strains from collection (bacteria, yeasts and moulds) and of an evaluation of the number of revivable microorganisms seven days after inoculation.

In order to demonstrate the effect of the antimicrobial mixture, the antimicrobial activity of a cosmetic formulation containing 0.05% of 4-(3-ethoxy-4-hydroxyphenyl)butan-2-one and 0.3% of chlorphenesin was compared with the same formula alone (control), after inoculation with about $10^6$ cfu (colony-forming units)/gram of cosmetic formulation.

Cosmetic Formulation

A facial care oil-in-water emulsion having the following composition was prepared (contents in weight percentages):
Sorbitan tristearate (Span 65 V from Croda) 0.9%
Glyceryl mono/distearate (36/64)/potassium stearate mixture
(Tegin Pellets from Goldschmidt) 3%
Polyethylene glycol stearate (40 ethylene oxide units) 2%
4-(3-Ethoxy-4-hydroxyphenyl)butan-2-one 0.05%
Chlorphenesin 0.3%
Propane-1,3-diol 3%
Mixture of mineral oil, microcrystalline wax and paraffin
(Vaseline Blanche Codex 236 from Aiglon) 4%
Liquid fraction of shea butter (Shea Olein from Olvea) 1%
Cyclopentadimethylsiloxane 5%
Cetyl alcohol 4%
Apricot kernel oil 0.3%
Hydrogenated polyisobutene (Parleam from NOF Corporation) 7.2%
Myristyl myristate 2%
Stearic acid 1.2%
Caffeine 0.1%
Citric acid 0.2%
Glycerol 3%
Sodium hydroxide 0.05%
Water qs 100%

Control formulation A: Formulation similar to the preceding one containing 0.05% of 4-(3-ethoxy-4-hydroxyphenyl)butan-2-one and without chlorphenesin (0.3% compensated with water)

Control formulation B: Similar formulation containing 0.3% of chlorphenesin and without 4-(3-ethoxy-4-hydroxyphenyl)butan-2-one (0.05% compensated with water)

Microorganism Cultures 5 pure cultures of microorganisms were used.

| MICROORGANISMS | Subculturing medium | T° | ATCC |
|---|---|---|---|
| *Escherichia coli* (Ec) | Trypto-casein soya | 35° C. | 8739 |
| *Enterococcus faecalis* (Ef) | Trypto-casein soya | 35° C. | 33186 |
| *Pseudomonas aeruginosa* (Pa) | Trypto-casein soya | 35° C. | 19429 |
| *Candida albicans* (Ca) | Sabouraud | 35° C. | 10231 |
| *Aspergillus niger* (An) | Malt | 35° C. | 6275 |

ATCC = American Type Culture Collection

The strains of gram-negative bacteria (*Escherichia coli* and *Pseudomonas aeruginosa*), gram-positive bacterium (*Enterococcus faecalis*), yeast (*Candida albicans*), and mould (*Aspergillus niger*) are inoculated into the subculturing medium, respectively the day before inoculation for the bacteria and the yeast, and 5 days before inoculation for the mould.

On the day of inoculation:
a suspension in tryptone salt diluent is prepared, respectively, for the bacteria and the yeast, so as to obtain by spectrophotometer a suspension with an optical density of between 35% and 45% of transmitted light at 544 nm;
for the mould, the spores are collected by washing the agar with 6 to 7 ml of harvesting solution and the suspension is recovered in a sterile tube or flask.

After homogenizing the microbial suspension, 0.2 ml of inoculum is introduced into each pill bottle (the suspensions are used pure: between $1 \times 10^8$ and $3 \times 10^8$ cfu per ml) and the microbial suspension in the 20 g of product (=cosmetic formulation) is homogenized thoroughly using a spatula.

The content of microorganisms present in the product corresponds after homogenization to a concentration of $10^6$ microorganisms per gram of product, i.e. inoculation to 1% of an inoculum containing $10^8$ microorganisms per ml.

After 7 days of contact time between the microorganisms and the product at 22° C.±2° C. and in the dark, ten-fold dilutions are performed and the number of revivable microorganisms remaining in the product is counted.

| Results | | | | | |
|---|---|---|---|---|---|
| No. of CFU/gram of product at T7 days | | | | | |
| | E. coli | P. aeruginosa | E. faecalis | C. albicans | A. niger |
| Antimicrobial mixture | <200 | <200 | <200 | <200 | <200 |

<200 CFU: sensitivity threshold of the method

The invention claimed is:

1. An antimicrobial mixture comprising 4-(3-ethoxy-4-hydroxyphenyl)butan-2-one and chlorphenesin.

2. The antimicrobial mixture according to claim 1, which comprises 4-(3-ethoxy-4-hydroxyphenyl)butan-2-one and chlorphenesin in amounts such that the 4-(3-ethoxy-4-hydroxyphenyl)butan-2-one/chlorphenesin weight ratio ranges from 0.1 to 0.9.

3. The antimicrobial mixture according to claim 1, which has antimicrobial activity on moulds.

4. A composition comprising, in a physiologically acceptable medium, an antimicrobial mixture according to claim 1.

5. The composition according to claim 4, which comprises at least one additional ingredient chosen from water, oils, polyols containing from 2 to 10 carbon atoms, gelling agents, surfactants, film-forming polymers, dyestuffs, fragrances, fillers, UV-screening agents, plant extracts, cosmetic and dermatological active agents, and salts.

6. The composition according to claim 4, wherein the 4-(3-ethoxy-4-hydroxyphenyl)butan-2-one is present in a content ranging from 0.01% to 5% by weight relative to the total weight of the composition.

7. The antimicrobial mixture according to claim 1, which has antimicrobial activity on *Aspergillus niger*.

8. The antimicrobial mixture according to claim 2, which has antimicrobial activity on *Aspergillus niger*.

9. The antimicrobial mixture according to claim 2, which has antimicrobial activity on moulds.

10. A composition comprising, in a physiologically acceptable medium, an antimicrobial mixture according to claim 2.

11. A composition comprising, in a physiologically acceptable medium, an antimicrobial mixture according to claim 3.

12. The composition according to claim 5, wherein the 4-(3-ethoxy-4-hydroxyphenyl)butan-2-one is present in a content ranging from 0.01% to 5% by weight relative to the total weight of the composition.

13. The antimicrobial mixture according to claim 1, which comprises 4-(3-ethoxy-4-hydroxyphenyl)butan-2-one and chlorphenesin in amounts such that the 4-(3-ethoxy-4-hydroxyphenyl)butan-2-one/chlorphenesin weight ratio ranges from 0.1 to 0.7.

14. The antimicrobial mixture according to claim 1, which comprises 4-(3-ethoxy-4-hydroxyphenyl)butan-2-one and chlorphenesin in amounts such that the 4-(3-ethoxy-4-hydroxyphenyl)butan-2-one/chlorphenesin weight ratio ranges from 0.15 to 0.6.

15. A composition comprising, in a physiologically acceptable medium, an antimicrobial mixture according to claim 3.

16. The composition according to claim 5, wherein the 4-(3-ethoxy-4-hydroxyphenyl)butan-2-one is present in a content ranging from 0.01% to 5% by weight relative to the total weight of the composition.

17. The composition according to claim 4, wherein the 4-(3-ethoxy-4-hydroxyphenyl)butan-2-one is present in a content ranging from 0.01% to 3% by weight relative to the total weight of the composition.

18. The composition according to claim 4, wherein the 4-(3-ethoxy-4-hydroxyphenyl)butan-2-one is present in a content ranging from 0.01% to 2.5% by weight relative to the total weight of the composition.

19. A composition comprising, in a physiologically acceptable medium, an antimicrobial mixture according to claim 13, wherein the 4-(3-ethoxy-4-hydroxyphenyl)butan-2-one is present in a content ranging from 0.01% to 5% by weight relative to the total weight of the composition.

20. A composition comprising, in a physiologically acceptable medium, an antimicrobial mixture according to claim 14, wherein the 4-(3-ethoxy-4-hydroxyphenyl)butan-2-one is present in a content ranging from 0.01% to 5% by weight relative to the total weight of the composition.

* * * * *